US00PP21074P2

(12) United States Plant Patent
Aguas et al.

(10) Patent No.: US PP21,074 P2
(45) Date of Patent: Jun. 22, 2010

(54) RASPBERRY PLANT NAMED 'PACIFIC DELUXE'

(50) Latin Name: ***Rubus idaeus* L.**
Varietal Denomination: Pacific Deluxe

(75) Inventors: Mario Aguas, Freedom, CA (US); Thomas Amrhein, Watsonville, CA (US); Jose Lopez Medina, Michoacan (MX)

(73) Assignee: Pacific Berry Breeding, LLC, Salinas, CA (US)

( * ) Notice: Subject to any disclaimer, the term of this patent is extended or adjusted under 35 U.S.C. 154(b) by 0 days.

(21) Appl. No.: 12/316,346

(22) Filed: Dec. 11, 2008

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent L Bell
(74) *Attorney, Agent, or Firm*—Jondle & Associates, P.C.

(57) ABSTRACT

'Pacific Deluxe' is a new raspberry cultivar particularly distinguished by having large fruit throughout the season, bright color, excellent post-harvest quality and resistance to *Phytophthora rubi*, is disclosed.

1 Drawing Sheet

Genus and species: *Rubus idaeus* L.
Variety denomination: 'Pacific Deluxe'.

BACKGROUND OF THE NEW PLANT

This invention relates to a new and distinct variety of raspberry (*Rubus idaeus* L.) plant named 'Pacific Deluxe'. 'Pacific Deluxe' originated as a seedling from the cross between the proprietary female raspberry parent '401' (unpatented) with the proprietary male raspberry parent '433' (unpatented) made in April 2003 in Oxnard, Calif.

The new cultivar was first propagated via vegetative cuttings and tissue culture in Watsonville, Calif. in June 2007 and has been asexually reproduced repeatedly by vegetative cuttings and tissue culture in Watsonville, Calif. for two generations. The present invention has been found to retain its distinctive characteristics through successive asexual propagations.

Plant Breeder's Rights for this cultivar have not been applied for prior to the filing of this application. 'Pacific Deluxe' has not been made publicly available more than one year prior to the filing of this application.

SUMMARY OF THE INVENTION

The following are the most outstanding and distinguishing characteristics of this new cultivar when grown under normal horticultural practices in Watsonville, Calif.

1. Large fruit throughout the harvest season;
2. Bright color;
3. Excellent post-harvest quality; and
4. Resistance to *Phytophthora rubi*.

DESCRIPTION OF THE PHOTOGRAPH

This new raspberry plant is illustrated by the accompanying photograph which shows a close-up of the plant's berry, canes and foliage from an 8 month-old plant in Watsonville, Calif. The colors shown are as true as can be reasonably obtained by conventional photographic procedures.

DESCRIPTION OF THE NEW CULTIVAR

The following detailed description sets forth the distinctive characteristics of 'Pacific Deluxe'. The data which define these characteristics were collected from asexual reproductions carried out in Watsonville, Calif. The plant history was taken on 1-and one-half year-old plants in August 2008. The following descriptions relate to plants grown in a field in Watsonville, Calif. Color references are to The R.H.S. Colour Chart of The Royal Horticultural Society of London (R.H.S.), 4$^{th}$ Edition.

DETAILED BOTANICAL DESCRIPTION

Classification:
- *Family.*—Rosaceae.
- *Botanical.*—*Rubus idaeus* L.
- *Common name.*—Raspberry.

Parentage:
- *Female parent.*—'401', a proprietary raspberry plant (unpatented).
- *Male parent.*—'433', a proprietary raspberry plant (unpatented).

Plant:
- *Form and habit.*—Erect growth habit; primocane fruiting; canes grow to about 1.5 m before terminating in an inflorescence.
- *Height (measured from crown to apex).*—120 cm to 160 cm.
- *Spread (measured from leaf tip to leaf tip).*—39.6 cm.
- *How propagated.*—Root cuttings.
- *Time to initiate and develop roots.*—60 days.
- *Root description.*—Fibrous.
- *Root diameter.*—0.2 cm.

Primocanes:
- *Diameter.*—1.01 cm.
- *Length.*—120 cm to 160 cm.
- *Number of nodes.*—25 to 35.
- *Internode length.*—4.8 cm.
- *Number of canes/hill.*—4 to 6.
- *Cane color.*—RHS 146D.

*Spine.*—Present. Spine color: RHS 59A. Spines/unit area: 6 $cm^2$. Spine shape: Acuminate. Spine length: 0.1 cm. Spine width: 0.02 cm. Spine apex: Acuminate.

Floricanes:

*Diameter.*—1.0 cm to 1.2 cm.
*Length.*—62 cm.
*Number of nodes.*—16.
*Internode length.*—5.6 cm.
*Cane color.*—RHS 178A.

Leaves:

*Terminal leaflet.*—Cordate, lobed.
*Arrangement.*—Alternate.
*Size of terminal leaflet.*—Length: 11 cm. Width: 9 cm.
*Shape of apex.*—Cuspidate.
*Shape of base.*—Cordate.
*Margin.*—Doubly-serrate.
*Texture.*—Glabrous.
*Number of serrations/leaf.*—97 to 109.
*Shape of serrations.*—Doubly-serrate; pointed.
*Venation pattern.*—Palmate.
*Venation color.*—Upper surface: RHS 144B. Lower surface: RHS 194B.
*Number of leaflets/leaf.*—3 to 5.
*Glossiness.*—Present.
*Primocane leaves.*—Color: Upper surface: RHS 137A. Lower surface: RHS 189B. Petiole length: 5.5 cm. Petiole diameter: 0.32 cm. Petiole color (upper): RHS 176C (Greyed-Orange). Petiole color (lower): RHS 144C (Yellow-Green). Rachis length: 6.0 cm. Rachis diameter: 0.21 cm. Rachis color (upper): RHS 176B (Greyed-Orange). Rachis color (lower): RHS 154C (Yellow-Green). Stipule length: 1.0 cm. Stipule width: 0.08 cm. Stipule number per leaf: 2. Stipule color: RHS 144B (Yellow-Green).
*Terminal leaflet.*—Length: 11 cm. Width: 9 cm. Petiolule length: 2 cm Petiolule diameter: 0.2 cm. Petiolule color (upper): RHS 176B (Greyed-Orange). Petiolule color (lower): RHS 154C (Yellow-Green).
*Distal lateral leaflet.*—Length: 9 cm. Width: 7 cm. Petiolule length: 2 cm. Petiolule diameter: 0.2 cm. Petiolule color (upper): RHS 176B (Greyed-Orange). Petiolule color (lower): RHS 154C (Yellow-Green).
*Basal lateral leaflet.*—Length: 12 cm. Width: 9.5 cm. Petiolule length: 2 cm. Petiolule diameter: 0.2 cm. Petiolule color (upper): RHS 176B (Greyed-Orange). Petiolule color (lower): RHS 154C (Yellow-Green).

Flowers:

*Bud.*—Shape: Acute. Length: 0.4 cm. Diameter (base): 0.5 cm. Diameter (tip): 0.15 cm. Color: RHS 146D (Yellow-Green).
*Time of flowering* (50% *of plants at first flower*).—Early August on primocanes.
*Size.*—Length: 0.8 cm. Diameter: 2 cm.
*Fragrance.*—None.
*Color.*—RHS 155B.
*Peduncle.*—Length: 10 cm to 12 cm. Diameter: 0.2 cm. Color: RHS 146A. Pubescence: Present.
*Petal.*—Petal number per flower: 5. Petal shape: Obtuse. Petal length: 0.9 cm. Petal width: 0.5 cm. Petal apex: Obtuse. Petal base: Acute. Petal margin: Entire. Color (both upper and lower surfaces): RHS 155B (White).
*Flowering trusses shape.*—Flattened with rounded edges.
*Sepal.*—Quantity: 5. Length: 0.9 cm. Width: 0.5 cm. Sepal apex: Acuminate. Sepal margin: Entire. Color: RHS 146C.
*Pedicel.*—Color: RHS 146C. Length: 1.0 cm. Pedicel diameter: 0.22 cm.

Reproductive organs:

*Self Fertile.*—Yes.
*Stamens* (*number*).—64.
*Filament.*—Length: 0.7 cm. Diameter: 0.1 cm.
*Stamen color.*—RHS 155A.
*Anthers.*—Color (post dehiscence): RHS 165A. Length: 0.1 cm. Diameter: 0.05 cm.
*Pollen color.*—RHS 155A.
*Pollen amount.*—Moderate.
*Style.*—Length: 0.5 cm. Diameter: 0.1 cm. Color: RHS 155A.
*Stigma.*—Length:0.02 cm. Diameter: 0.01 cm. Color: RHS 158A.

Fruit:

*Predominant shape.*—Conical.
*Weight* (*per berry*).—6 g to 8 g.
*Berry brix.*—10.0.
*Size.*—Length: 2.5 cm. Width: 2.0 cm.
*Receptacle.*—Diameter: 1.5 cm. Length: 0.9 cm. Color: RHS 4D (Yellow).
*Drupelet.*—Diameter: 0.3 cm. Width: 0.3 cm. Number: 90 to 110. Weight: 0.02 g.
*Color of mature fruit.*—External: RHS 35A. Internal: RHS 35C.
*Firmness of skin.*—Very firm.
*Firmness of flesh.*—Very firm.
*Hollow center.*—Yes.
*Number of fruit per node.*—4 to 8.
*Time of ripening* (50% *of plants with first ripe fruit*).—Mid-September on primocanes.
*Time of fruiting.*—Floricanes: Spring. Primocanes: Late summer to fall.
*Type of bearing.*—Both on previous year's canes in summer and current year's canes in autumn.
*Fruit yield.*—1.5 Kg/plant.
*Market use.*—Fresh.
*Keeping quality.*—Excellent.
*Shipping quality.*—Excellent.

Resistance to diseases, insects and mites: Resistant to *Phytophthora rubi*, atypical of species.

COMPARISON WITH PARENTAL AND KNOWN CULTIVARS

'Pacific Deluxe' differs from the proprietary female raspberry parent '401' in that 'Pacific Deluxe' has larger fruit than 401.

'Pacific Deluxe' differs from the male raspberry parent '433' in that ' Pacific Deluxe' is more vigorous and has a higher fruit yield than '433'.

'Pacific Deluxe' differs from the commercial variety 'Caroline' (U.S. Plant Pat. No. 10,412) in that 'Pacific Deluxe' has larger fruit with firmer flesh than 'Caroline'.

We claim:

1. A new and distinct cultivar of raspberry plant as shown and described herein.

* * * * *

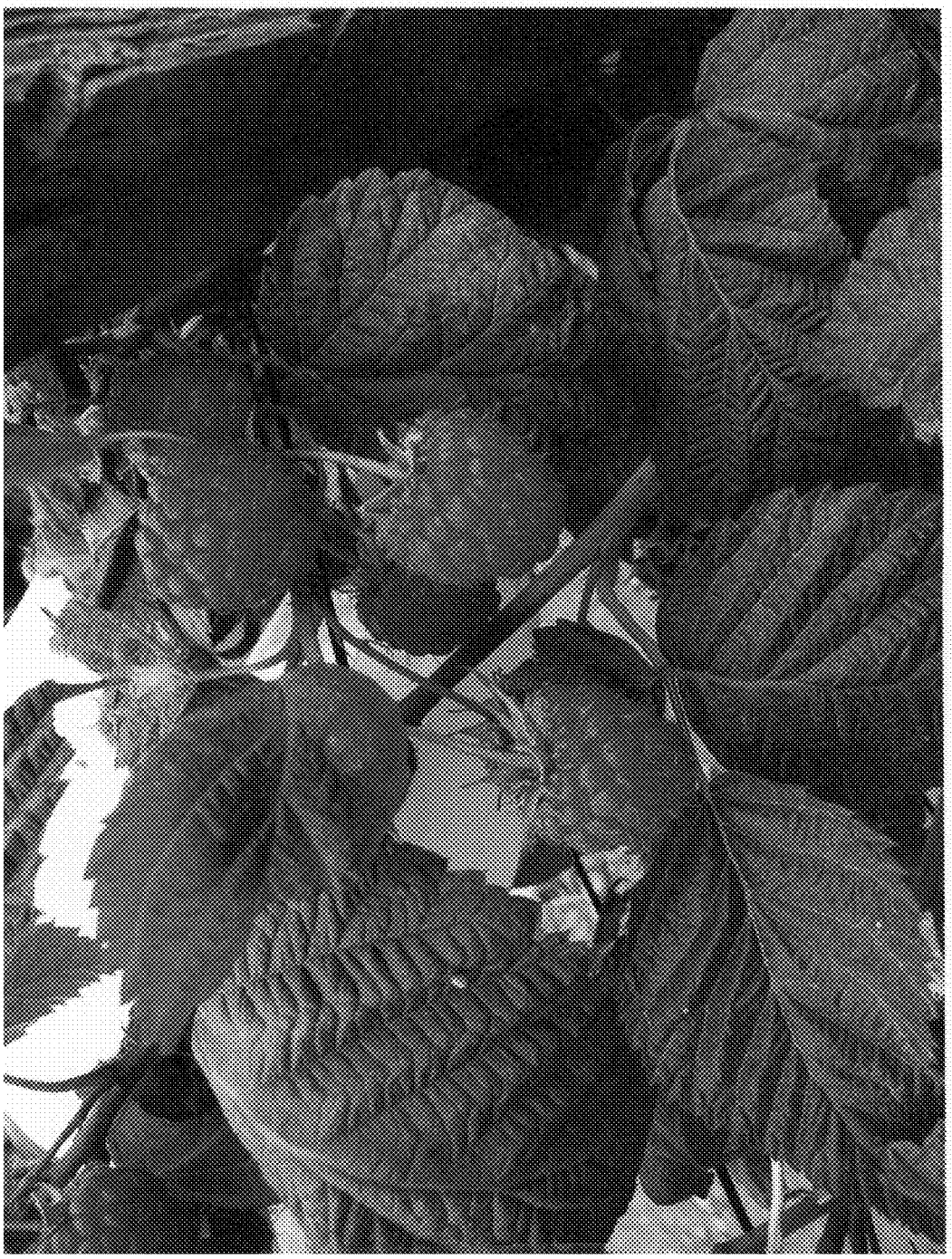

UNITED STATES PATENT AND TRADEMARK OFFICE

CERTIFICATE OF CORRECTION

PATENT NO. : PP21,074 P2
APPLICATION NO. : 12/316346
DATED : June 22, 2010
INVENTOR(S) : Mario Aguas et al.

It is certified that error appears in the above-identified patent and that said Letters Patent is hereby corrected as shown below:

Col. 1, lines 8 through 11, change "from the cross between the proprietary female raspberry parent '401' (unpatented) with the proprietary male raspberry parent '433' (unpatented) made in April 2003 in Oxnard, Calif." to read as --from a cross between an unknown female raspberry plant and an unknown male raspberry plant in 2003.--.
Col. 2, lines 19 through 23, delete "Parentage: Female parent: '401', a proprietary raspberry plant (unpatented). Male parent: '433', a proprietary raspberry plant (unpatented).".
Col. 4, lines 47 through 48, change "COMPARISON WITH PARENTAL AND KNOWN CULTIVARS" to read as --COMPARISON WITH KNOWN CULTIVARS--.
Col. 4, lines 50 and 51, change "the proprietary female raspberry parent '401'" to read as --the raspberry plant '401'--.
Col. 4, lines 53 through 54, change "the male raspberry parent '433'" to read as --the raspberry plant '433'--.
Col. 4, following line 58, add --The parental lines are no longer available for comparison.--.

Signed and Sealed this
Sixteenth Day of August, 2011

David J. Kappos

David J. Kappos
*Director of the United States Patent and Trademark Office*